Figure 1:
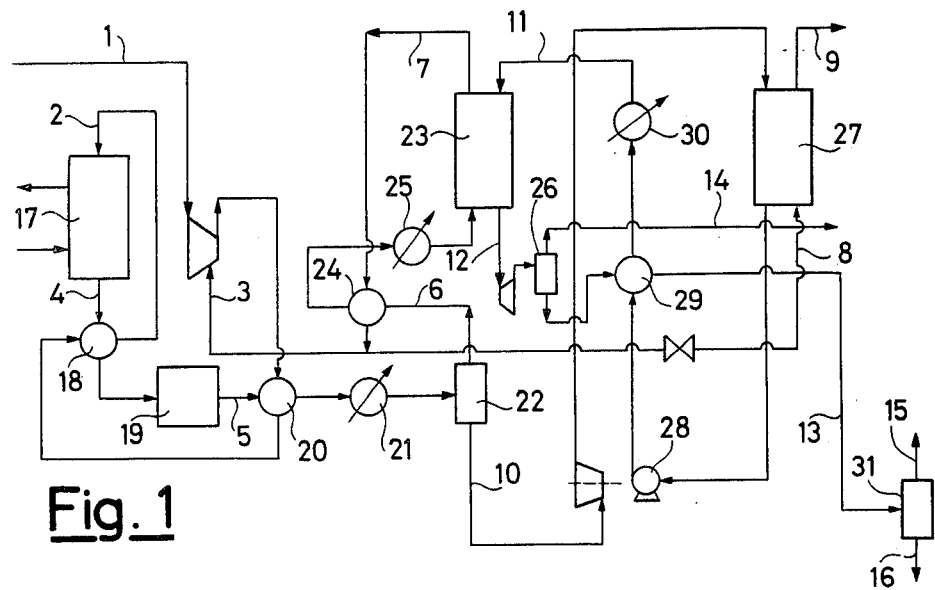

United States Patent [19]

Di Pietro et al.

[11] Patent Number: 4,460,378
[45] Date of Patent: Jul. 17, 1984

[54] PROCESS FOR THE PRODUCTION OF A "FUEL GRADE" MIXTURE OF METHANOL AND HIGHER ALCOHOLS

[75] Inventors: Raffaele Di Pietro, Milan; Alberto Paggini, Spino D'Adda; Vincenzo Lagana', Milan, all of Italy

[73] Assignee: Snamprogetti S.p.A., Milan, Italy

[21] Appl. No.: 514,546

[22] Filed: Jul. 18, 1983

Related U.S. Application Data

[63] Continuation of Ser. No. 269,709, Jun. 2, 1981, , which is a continuation-in-part of Ser. No. 215,173, Dec. 11, 1980, abandoned.

[30] Foreign Application Priority Data

May 16, 1980 [IT] Italy .............................. 22117 A/80

[51] Int. Cl.³ .............................................. C10L 1/18
[52] U.S. Cl. ..................................... 44/54; 44/53; 518/704; 518/713; 518/714; 518/728; 203/43
[58] Field of Search ...................... 44/53, 54; 578/704, 578/713, 714, 728; 203/43

[56] References Cited

U.S. PATENT DOCUMENTS

| | | | |
|---|---|---|---|
| 1,569,775 | 1/1926 | Mittasch | 518/713 |
| 1,791,568 | 2/1931 | Mittasch | 518/713 |
| 2,010,005 | 8/1935 | Berliner | 44/54 |
| 2,281,228 | 4/1942 | Brown | 518/713 |
| 3,763,205 | 10/1973 | Green | 518/713 |
| 3,940,428 | 2/1976 | Connell | 518/705 |
| 3,950,369 | 4/1976 | Gent | 518/713 |

Primary Examiner—Jacqueline V. Howard
Attorney, Agent, or Firm—Morgan, Finnegan, Pine, Foley & Lee

[57] ABSTRACT

A process for the production of a "fuel grade" mixture of methanol and higher alcohols from CO and $H_2$.

To reduce the amount of water contained in the mixture coming from the synthesis reactor of the alcohol synthesis the reaction product is cooled and fed to a secondary reactor wherein the reaction of conversion:

$$CO + H_2O \rightleftharpoons CO_2 + H_2$$

is conducted in conditions near to equilibrium.

The further reaction product is cooled down further so as to obtain a liquid phase constituted by the alcohols, and in which there are still dissolved some gases, and a gaseous phase containing the carbon dioxide produced in the secondary reactor together with the non-reacted gases. The gaseous phase is sent to a section of absorption of the $CO_2$ wherein the absorbing liquid is constituted by the very alcoholic mixture produced; after removal of the $CO_2$ the gas is partly recycled and partly let off in order to avoid the accumulation of inert gases contained in the feeding mixture.

Before being used in the section of absorption of the $CO_2$, the alcoholic mixture is sent into a stripping column to remove the gases dissolved therein; the let off gases are used as stripping agents.

In the secondary reactor of conversion operation is carried out at a temperature comprised between 150° C. and 250° C., at a pressure equal to that of the synthesis reactor and in the presence of a copper catalyst.

16 Claims, 2 Drawing Figures

PROCESS FOR THE PRODUCTION OF A "FUEL GRADE" MIXTURE OF METHANOL AND HIGHER ALCOHOLS

The present application is a continuation of Ser. No. 269,709, filed June 2, 1981 whih, in turn, is a continuation-in-part application of Ser. No. 215,173, filed Dec. 11, 1980, now abandoned.

The instant invention concerns a process for the production of a "fuel grade" mixture of methanol and higher alcohols.

It is known that methanol may be employed alone, or in admixture with gasoline, as a fuel.

It has been found that the use of methanol in admixture with gasoline is made prohibitive by the amount of water that is present both in the refining plants and in the circuit of distribution of the fuel: at low temperature and in the presence of smallest amounts of water the methanol tends to unmix forming an aqueous phase rich with methanol and a hydrocarbon phase, thereby rendering its use unadvisable.

It is known that this inconvenience may be overcome by the use of suitable solubilizers, in particular the $C_2$, $C_3$, $C_4$, $C_5$, $C_6$ alcohols have been indicated.

These alcohols may be produced separately (they are to be found in the trade but at high prices) and added to methanol or they may be co-produced together with methanol and the latter solution is deemed to be cheaper.

As a matter of fact it is known that by conveniently modifying the catalysts for methanol production, both those of the high temperature process, of Zn, Cr type, and those of the lower temperature process, of Cu type, it is possible to obtain from hydrogen and carbon monoxide a mixture of methanol, higher alcohols and water contemporaneously.

Water is produced in the reaction forming higher alcohols $$2CO + 4H_2 \rightleftarrows C_2H_5OH + H_2O \quad (1)$$

$$3CO + 6H_2 \rightleftarrows C_3H_7OH + 2H_2O \quad (2)$$

$$4CO + 8H_2 \rightleftarrows C_4H_9OH + 3H_2O \quad (3)$$

as well as in the reaction forming methanol from $CO_2$, which may possibly be present in the feed:

$$CO_2 + 3H_2 \rightleftarrows CH_3OH + H_2O \quad (4)$$

Since, as we have seen, the function of the higher alcohols is to keep the methanol in solution in the gasoline in the presence of water, it is important, in order not to add fresh water to the system, that the mixture of methanol and higher alcohols should contain the least possible amount of water.

By a "fuel grade" mixture of methanol and higher alcohols it is just intended a mixture meeting these requirements, namely that the amount of water admissible should be of the order of a thousand ppm.

The $C_2$, $C_3$, $C_4$, $C_5$ higher alcohols from azeotropes with water and, therefore, lowering the water content from the level of some %, as present in the mixture after the cooling and condensing of the gas, down to the level of a thousand ppp as requeste by the fuel grade is a difficult and costly operation.

Present technique teaches to separate the water from that mixture by means of an azeotropic distillation using cyclohexane, benzene or other azeotropic agents.

Now it has surprisingly been found that it is possible to obtain a mixture of methanol and higher alcohols of fuel grade from carbon monoxide and hydrogen, already after the cooling and the condensation of the reacted gas, thereby avoiding the necessity of resorting to the stage of azeotropic distillation which is very burdensome both owing to investment cost and to energy consumption.

It is an object of the present invention to provide a process for producing a mixture of methanol and higher alcohols of fuel grade comprising:

(a) feeding to a synthesis reactor a gaseous mixture essentially constituted by CO and $H_2$;
(b) cooling the reaction mixture constituted by methanol, higher alcohols, water and unreacted gases;
(c) sending the latter to a conversion reactor;
(d) cooling the further product of reaction constituted by methanol, higher alcohols, unreacted gases, carbon dioxide and traces of water;
(e) separating a liquid phase constituted by the "fuel grade" alcoholic mixture and a gaseous phase essentially constituted by CO, $H_2$ and $CO_2$;
(f) sending the gaseous phase to a section of absorption for the removal of the $CO_2$, the gas so purified being recycled in part and discharged in part in order to avoid the accumulation of inert substances;
(g) sending the liquid phase to a stripping section in order to remove the gases dissolved therein, using the discharged gases as stripping agents;
(h) sending the liquid phase so purified to the absorption section where it is utilized as an absorbing liquid.

More particularly the object of the present invention is to provide a process for producing an alcoholic mixture of fuel grade according to which the mixture of reacted gases leaving the synthesis reactor is fed after cooling to a second reactor where on a conversion catalyst of conventional kind the reaction $$CO + H_2O \rightleftarrows CO_2 + H_2 \quad (5)$$

is carried on in conditions near to equilibrium.

This solution, which can be adopted also with only one reactor, permits to reduce the amount of water, produced according to the reactions (1), (2), (3) and (4), to such values that if the reacted gas is cooled and the condensed product is separated from the gaseous phase, in the liquid there remains only an amount of $H_2O$ at a level of a thousand ppm (fuel grade mixture).

Since the conversion on passage is low, it is necessary to recycle the gas that has not reacted to the synthesis reactor, as well as to discharge a portion of the gas so as to avoid the accumulation of inert substance.

Owing to the recycle the $CO_2$ produced according to the reaction (5) would be fed back to the reactor, whence it is necessary to resort to its removal in order to get the same situation at every passage.

It is a further object of the instant invention to provide a process for the production of methanol and higher alcohols, of fuel grade, that involves the use, as a solution absorbing the carbon dioxide, of the alcoholic mixture produced, whilst the let off gas is employed to strip the gases dissolved in the very absorbing solution.

According to the process of the instant invention the synthesis gas, mainly containing CO and $H_2$ and traces of $CO_2$, $N_2$ and $CH_4$, is sent to the synthesis reactor for the production of methanol and higher alcohols.

The synthesis reactor can operate both at high pressure and at low pressure, whence in the former case the preparation of the alcoholic mixture takes place at a temperature that generally is comprised between 300° C. and 500° C., preferably between 360° C. and 420° C., and at a pressure higher than 150 ata, preferably higher than 200 ata; in the latter case the preparation takes place at a temperature comprised between 200° C. and 300° C., preferably between 230° C. and 270° C., and at a pressure comprised between 30 and 150 ata, preferably between 50 and 100 ata.

The catalysts are those used and adapted for the production of methanol and more particularly of the type of zinc, chromium in the former case, and of the type of copper, zinc, with Al and/or Cr and/or V and/or Mn in the latter case, properly modified with alkali metals and/or alkaline earth metals to encourage the synthesis of the higher alcohols.

From the synthesis reactor the gaseous mixture is sent after previous cooling with heat recovery, to a conversion reactor where, in the presence of a copper catalyst, the reaction (5) is carried on in conditions near to its equilibrium.

In the conversion reactor the pressure is equal to that of the synthesis reactor whilst the temperature is sensibly lower and is comprised between 150° C. and 250° C., preferably between 160° C. and 220° C.

At the outlet of the conversion reactor the reacted gaseous mixture is cooled, first in a heat recuperator and then in a water or air condenser, recovering a condensed product that is separated from the gas.

The gas is cooled by a low temperature frigorific cycle and passes into an absorption column, whereafter a portion is recycled to the synthesis reactor whilst another portion (the discharge) is sent to a second column where the absorbing solution is prepared.

The liquid separated from the gas at the outlet of the reactor contains an amount of dissolved gases relative to the temperature and to the pressure of the condenser outlet. Hence in these conditions the liquid is not able to absorb all of the $CO_2$ on the recycle gas whence a stripping at lower pressure is needed.

This latter operation is carried out in a special column of desorption to the head of which is sent the liquid, while to the bottom there is sent the discharge gas, this column will have to work at a pressure lower than the synthesis pressure. The liquid free from $CO_2$ is taken over by a special pump from the desorption column; it is cooled and then it is sent to the head of the absorption column, that operates at the synthesis pressure.

At the bottom of this column enters the recycle gas with the $CO_2$; hence the liquid passing in countercurrent to the gas, absorbs all of the $CO_2$ therein contained, whence the gas leaving this column has few ppm of $CO_2$, whilst the liquid now contains all of the $CO_2$ that earlier was contained in the gas. The liquid is then freed from the $CO_2$ and from the other gases dissolved and is taken to a lower pressure or is recycled to the stripping column.

The flash of the liquid can be effected in a turbine and so the energy of compression can be recovered. Moreover it may happen that the gases separated and the discharge gas coming from the desorption column, be saturated with methanol vapour, whence it is adisable to provide recovery of the latter so as to eliminate losses.

In FIGS. (1) and (2) there are shown two flow sheets according to the process of the instant invention: according to FIG. 1 the synthesis gas (1) and the recycle gas (3) are brought to the operating pressure and fed through (2) to the reactor (17); the reaction product leaves the synthesis reactor with line (4) and after cooling in (18) it is sent to the conversion reactor (19) where its water content is sensibly reduced.

The reacted gas leaves the conversion reactor by means of line (5), it is sent first to the heat recuperator (20) then to the condenser (21) and then to the separator (22); from the head of the separator (22) there is recovered, through (6), a gaseous phase which is first cooled in the heat recuperator (24) and with a frigorific cycle (25) and is then sent to the section of absorption of the $CO_2$ (23).

From the head of the column (23) there is taken by (7) the gas free from $CO_2$ that in part is recycled to the synthesis with (3) and in part is discharged and sent with (8) to the column (27) where there is prepared the absorbing solution to be sent to the column (23).

From the basis of the separator (22) there is recovered, through (10), a liquid phase constituted by the fuel grade alcoholic mixture, that is utilized as an absorbing fluid in the column (23).

Since this liquid contains still some dissolved gas, it is sent to the stripping column (27) to which through (8) there arrive the discharge gases as stripping agents which then are discharged with (9).

From the column (27) there is taken the purified liquid by means of the pump (28) and the line (11) and said liquid is sent, after cooling in (29) and (30), to the absorption column (23).

From the bottom of this column there is discharged with (12) the alcoholic mixture containing almost all of the carbon dioxide previously contained in the recycle gas and now dissolved; the liquid is regenerated and freed from the $CO_2$ and from other gases dissolved, by means of expansion in a turbine, and is collected in the separator (26) from the head of which there is discharged with (14) the carbon dioxide together with the other gases; the liquid that may still contain some traces of $CO_2$ is preheated in (29) and is finally sent with (13) to the separator (31) from the bottom of which there is obtained with (16) the alcoholic mixture of fuel grade desired whilst from the head there are discharged with (15) the last traces of $CO_2$.

Moreover it may happen that in the discharged (9), (14) and (15) there be present relevant amounts of methanol whence it may be advisable to recover the latter in order to avoid losses; this recovery ought to be carried out in a special section which for the sake of simplicity is not represented in the drawing also because it does not form part of the instant invention.

Figure 2:
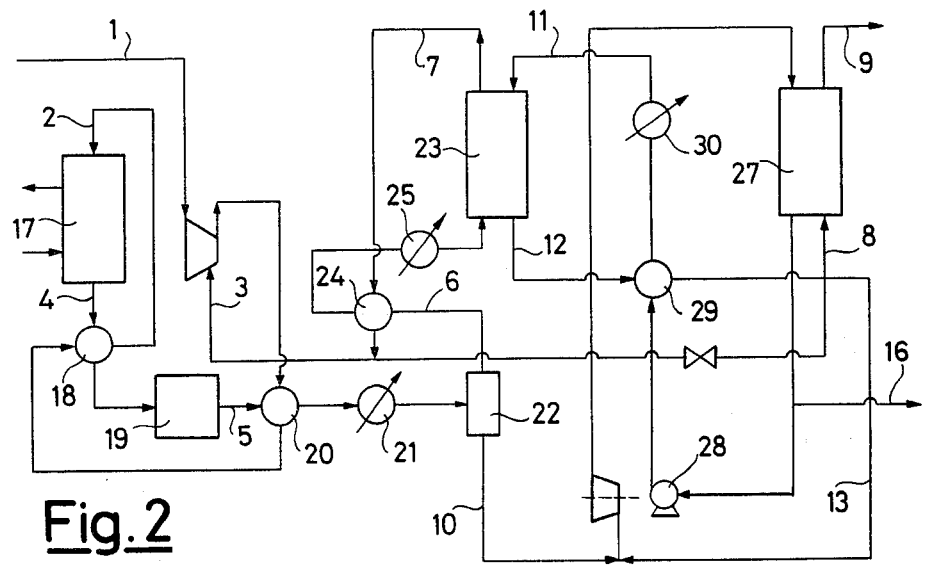

According to FIG. 2 the alcoholic mixture leaving the absorber (23) is regenerated by recycling it to the stripper (27); in this case the stream (12) joins the stream (10) and is sent, together with the latter, to the stripping stage.

The liquid leaving the basis of the column (27) is in part discharged with (16) and is in part recycled to the absorption column (23).

Now an example will be given having the purpose of better illustrating the invention, however, without limiting its scope.

It should be observed that the liquid mixture of methanol and higher alcohols as obtained with the process according to this invention has a limpidity which is comparable to that of the commercial gasolines, absence of dyestuffs and of unpleasant smells which are experienced, for example, in the alcohol mixtures as obtained with the Fischer-Tropsch synthesis.

EXAMPLE

Operation is carried out as shown in the flow sheet of FIG. 1; to the synthesis reactor there is fed, together with the recycle gas, a gaseous mixture constituted by:

|  | $Nm^3/h$ | % by vol. |
|---|---|---|
| CO | 6055.90 | 41.30 |
| $CO_2$ | 0.27 | traces |
| $H_2$ | 8509.20 | 58.10 |
| $N_2$ | 55.72 | 0.38 |
| $CH_4$ | 18.30 | 0.12 |

Synthesis Reaction

The catalyst has the following composition:
ZnO 27.1% by wt.; $Cr_2O_3$, 25.9% and $K_2O$: 2.0%. Catalyst: 10 cubic meters are used. Temp. 410° C., pressure 260 atm. The composition at point (2) of the flowsheet FIG. 1 is as follows:

| CO = 46.985% by vol. | 33190.4 Nor. Cu. Meters an Hour |
|---|---|
| $CO_2$ = 0.04% | 30 |
| $H_2$ = 46.985% | 33190.4 |
| $N_2$ = 5.14% | 3636.1 |
| $CH_4$ = 0.85% | 601.1 |
| $CH_3OH$ Traces | Traces Total 70648.82 Nor. Cu. Meters an Hour |
| GHSV = 7064.9/Hour | |

Conversion Reaction

Twenty Cu. Meters of catalyst are used, which has the following composition, by weight: ZnO—31.4%, $Cr_2O_3$=49.9%, Cu Oxide—18.7% GHSV: 3073.4/Hour, pressure 260 atm., temp. 200° C.

After the synthesis reaction and the conversion reaction there is obtained a product constituted by:

|  | $Nm_3/h$ | % by vol. |
|---|---|---|
| CO | 27599.20 | 44.84 |
| $CO_2$ | 1031.70 | 1.68 |
| $H_2$ | 25013.10 | 40.80 |
| $N_2$ | 3636.10 | 5.92 |
| $CH_4$ | 601.10 | 0.97 |
| $CH_3OH$ | 3159.82 | 5.10 |
| $CH_2H_5OH$ | 67.24 | 0.11 |
| $CH_3H_7OH$ | 119.50 | 0.19 |
| $CH_4H_9OH$ | 234.38 | 0.38 |
| $H_2O$ | 7.68 | 0.01 |

This product of reaction is cooled to provide a liquid phase and a gaseous phase; the liquid phase, containing still some gases dissolved, is sent to the stripper, while the gaseous phase is sent to the column of absorption of the $CO_2$.

To this column there arrives the purified liquid phase which leaves with the following composition:

|  | kg/h | % by weight |
|---|---|---|
| CO | 118.70 | 1.52 |
| $CO_2$ | 1859.50 | 24.02 |
| $H_2$ | 4.46 | 0.05 |
| $N_2$ | 15.00 | 0.19 |
| $CH_4$ | 7.14 | 0.09 |
| $CH_3OH$ | 4500.00 | 58.12 |
| $C_2H_5OH$ | 138.00 | 1.78 |
| $C_3H_7OH$ | 320.00 | 4.16 |
| $C_4H_9OH$ | 773.80 | 9.99 |
| $H_2O$ | 6.16 | 0.08 | and which after having been brought to a lower pressure and having been collected in a separator, yields the fuel grade alcoholic mixture having the composition:

|  | kg/h | % by weight |
|---|---|---|
| $CO_2$ | 20 | 0.3 |
| $CH_3OH$ | 4500 | 78.3 |
| $C_2H_5OH$ | 138 | 2.4 |
| $C_3H_7OH$ | 320 | 5.5 |
| $C_4H_9OH$ | 773.8 | 13.4 |
| $H_2O$ | 6.16 | 0.1 |

We claim:
1. In a process for producing fuel grade mixtures of methanol and higher alcohols, which process comprises:
   (a) feeding a gaseous mixture, consisting essentially of carbon monoxide and hydrogen to a synthesis reactor operating at a temperature of from 200° to 500° C. and at a pressure higher than 30 atm to form an intermediate product; and
   (b) cooling the intermediate product consisting of methanol, higher alcohols, water and unreacted gases,
the improvement which comprises:
   ($a^1$) subjecting the cooled intermediate product to the conversion reaction

$$CO + H_2O \rightarrow CO_2 + H_2,$$

operating said conversion process at a temperature of 150° to 250° C. and at the same pressure of the synthesis reactor to form a reaction product consisting essentially of methanol, higher alcohols, unreacted gases, carbon dioxide and traces of water;
   ($b^1$) cooling the reaction product to form liquid phase consisting essentially of the fuel mixture and a gaseous phase consisting essentially of CO, $H_2$ and $CO_2$;
   ($c^1$) separating the gaseous phase and then passing it into an absorption section for the elimination of $CO_2$, the gases so purified being in part recycled and in part let off to avoid the accumulation of inert matter;
   ($d^1$) sending the liquid phase to a stripping section to remove the gases dissolved therein, the let off gases of step ($c^1$) being used as stripping agents; and
   ($e^1$) sending the liquid phase so purified to the absorption section where it is utilized as an absorbing liquid.

2. A process according to claim 1 wherein the synthesis reactor is operated at a temperature comprised between 300° C. and 500° C.

3. A process according to claim 11 wherein the synthesis reactor is operated at a pressure higher than 150 ata.

4. A process according to claim 2 wherein the temperature is between 360° C. and 420° C.

5. A process according to claim 3 wherein the pressure is higher than 200 ata.

6. A process according to claim 1 wherein the synthesis reactor is operated at a temperature comprised between 200° C. and 300° C.

7. A process according to claim 1 wherein the synthesis reactor is operated at a pressure comprised between 30 and 150 ata.

8. A process according to claim 6 wherein the temperature is between 230° C. and 270° C.

9. A process according to claim 7 wherein the pressure is between 50 and 100 ata.

10. A process according to claim 1 wherein the temperature is between 160° C. and 220° C.

11. A process according to claim 1 wherein the conversion reactor is operated at the same pressure of the synthesis reactor.

12. A process according to claims 2 or 3 wherein the synthesis reaction takes place in the presence of a catalyst based on zinc and chromium modified with alkali metals and/or with alkaline earth metals.

13. A process according to claims 6 or 7 wherein the synthesis reaction takes place in the presence of a catalyst based on copper, zinc and with Al and/or Cr and/or V and/or Mn modified with Alkali Metals and/or Alkaline earth metals.

14. A process according to claims 10 or 12 wherein the conversion reaction takes place in the presence of a catalyst based on copper.

15. A process according to claim 1 wherein the absorbing liquid is regenerated and freed from the absorbed gases either by bringing it to a lower pressure or by recycling it to the stripping section.

16. A process according to claim 1 wherein the section of absorption of the $CO_2$ is operated at the same pressure of the synthesis reactor.

* * * * *